(12) United States Patent
Rudin et al.

(10) Patent No.: US 6,254,855 B1
(45) Date of Patent: Jul. 3, 2001

(54) METHOD FOR PRODUCING A SUSPENSION OF HYDROXYLAPATITE

(75) Inventors: Vsevolod Nikolaevich Rudin; Viktor Evgenievich Bozhevolnov; Vladislav Petrovich Zuev; Vladimir Fedorovich Komarov; Igor Vitallevich Melikhov; Vladimir Vasillevich Minaev; Andrei Yurlevich Orlov, all of Moscow (RU)

(73) Assignee: Aktsionernoe Obschestvo Zakrytogo Tipa "Ostim", Moscow (RU)

( * ) Notice: Subject to any disclaimer, the term of this patent is extended or adjusted under 35 U.S.C. 154(b) by 0 days.

(21) Appl. No.: 09/297,189
(22) PCT Filed: Oct. 29, 1997
(86) PCT No.: PCT/IB97/01414
§ 371 Date: Jun. 25, 1999
§ 102(e) Date: Jun. 25, 1999
(87) PCT Pub. No.: WO98/18719
PCT Pub. Date: May 7, 1998

(30) Foreign Application Priority Data

Oct. 31, 1996 (RU) ................................................ 96121322

(51) Int. Cl.⁷ ................................ A61K 9/68; A61K 7/16; A61K 7/021; A61K 9/00; A61F 13/00
(52) U.S. Cl. ................................ 424/48; 424/49; 424/63; 424/400; 424/435; 424/489
(58) Field of Search ..................................... 424/489, 400, 424/435, 48, 49, 63

(56) References Cited

U.S. PATENT DOCUMENTS

| 4,207,306 | * | 6/1980 | Jarcho ................................. 423/633 |
| 5,320,829 | * | 6/1994 | Garlich et al. .......................... 424/54 |
| 5,437,858 | * | 8/1995 | Hungerbach et al. ................. 424/53 |
| 5,439,680 | * | 8/1995 | Horikoshi et al. ................ 424/157.1 |

* cited by examiner

Primary Examiner—Thurman K. Page
Assistant Examiner—S. Tran

(57) ABSTRACT

An improved hydroxylapatite HAP composition is in the form of a suspension or paste. The improvement is that the composition may have a homogenous concentration in the range of from 7% to 96%. The invention is also concerned with a method for producing the homogeneous concentration compositions of HAP and their industrial applications.

22 Claims, 1 Drawing Sheet

TABLE

| No. | I t | I v | I C | II t | II v | II C | III t | III v | III C | IV t | IV v | IV C | V t | V v | V C |
|---|---|---|---|---|---|---|---|---|---|---|---|---|---|---|---|
| 1. | 7 | 0.9 | 16.3 YP | | | | | | | | | | | | |
| 2. | 5 | 0.8 | 12.5 | 8 | 1.2 | 22.3 YP | | | | | | | | | |
| 3. | 10 | 1.0 | 17.9 | 12 | 1.3 | 31.3 | 12 | 1.9 | 42.1 YP | | | | | | |
| 4. | 10 | 1.2 | 19.2 | 12 | 1.5 | 34.1 | 15 | 2.0 | 44.2 | 15 | 2.5 | 56.1 YP | | | |
| 5. | 7 | 0.8 | 14.8 | 10 | 1.2 | 26.6 | 10 | 2.0 | 39.9 | 15 | 2.5 | 56.6 | 25 | 3 | 75 YP |

PROCESSING STAGES

METHOD FOR PRODUCING A SUSPENSION OF HYDROXYLAPATITE

This application is a 371 of PCT/IB97/01414 filed Oct. 29, 1997.

FIELD OF THE INVENTION

The present invention is concerned with a hydroxylapatite composition having a homogeneous concentration within the range of from 7% to 96%. The present invention also relates to a method for preparing the hydroxylapatite compositions and products containing the hydroxylapatite compositions and its use in specific applications.

Hydroxylapatite (HAP) may be used in medicine as a denture material, prophylactic additive in tooth pastes and medicinal solutions, chewing gums, sorbents for medicinal preparations and various organic and inorganic compounds, in materials for stomatology and bone surgery and as a filler or sorbent agent for gas-liquid chromatography.

STATE OF THE ART

Due to the fields of application of hydroxylapatite the availability of pure HAP, free from other calcium phosphates has become the main requirement. Furthermore, it became highly desirable to prepare HAP not only in powder form but as a suspension or paste of a predetermined composition.

A known method for producing hydroxylapatite is based on the mixing of a suspension of calcium hydroxyde with an aqueous solution of phosphoric acid, wherein either the reaction product of both components or the mixture is treated by a grinding operation that ensures a mechano-chemical activation of the reagents. According to this method as a grinding apparatus there may be used mills and crushers of various types and as a grinding medium glass beads, aluminium balls and the like. According to this method hydroxylapatite having large crystals is mainly produced.

This method does not allow to produce fairly pure hydroxylapatite and moreover the preparation of suspensions and pastes from hydroxylapatite having large crystals is practically impossible (Patent of Japan No. 62-43524, 1987).

Furthermore, a method for producing hydroxylapatite is known from the Russion Federation patent application no. 93012609/26, filed on Mar. 9, 1993 which is forming the technical background of the present invention. According to this method a suspension of calcium hydroxide is reacted with phosphoric acid in a closed multiple circuit whereby the suspension of calcium hydroxide is past through two zones. In the first zone a continuous supply of phosphoric acid in the amount necessary to reach pH=10–11 is provided. The suspension flow rate in the first zone is 0.8 m/s to 1.5 m/s and the residence time is 1.0 s to 1.5 s. In the second zone the obtained mixture is diluted by 400 to 500 times with a suspension of calcium hydroxide. The diluted mixture is returned to the first zone and the process is repeated thereby ensuring a 4 to 5 fold circulation of the complete volume of the mixture during 10 to 20 min. After the feeding of acid is terminated the obtained suspension of the product is stirred for additionally 10 to 12 min. The resulting suspension of hydroxylapatite has a concentration of 4.5% to 5.0%. Additionally, the suspension may be dried to produce solid hydroxylapatite or dehydrated by centrifugation to produce a suspension of hydroxylapatite having a concentration of 18% to 33%.

This method ensures the production of a pure product with a desired composition and the yield is 99.5% to 99.8% of the theoretical one and increases the technological adaptability of the process.

A disadvantage of this known method, however, is that a suspension with homogeneous concentration can not be obtained.

The preparation of highly concentrated suspensions of more than 18% is time-consuming, requires large volumes of apparatus and the production of a suspension with a concentration higher than 33% is practically impossible.

DESCRIPTION OF THE INVENTION

The present invention is based on the problem to produce a suspension of hydroxylapatite with any necessary concentration, i.e. either less than 18% or more than 33% and as well pastes of hydroxylapatite having a homogeneous concentration composition.

According to the present invention a hydroxylapatite (HAP) composition is provided, wherein the dimensions of the hydroxylapatite particles is 0.01 $\mu$m to 0.02 $\mu$m in width and 0.05 $\mu$m to 0.1 $\mu$m length, the composition having a homogeneous concentration within the range of from 7% to 96%.

Preferred concentration ranges are given in subclaims 2 to 6. The composition may be in the form of a suspension or paste.

The hydroxylapatite (HAP) compositions of this invention are starting from a suspension of hydroxylapatite with a concentration of 4.5% to 5.0% which may be obtained preferably according to the method of the patent of the Russian Federation mentioned above. According to the invention, such a suspension is subjected to alternating stirring and filtration ranges with the stirring being carried out at a rate of 0.8 m/s to 3.0 m/s for 5 to 25 minutes and each stage is providing increasing homogeneous concentrations of hydroxylapatite due to increased stirring rates and/or times. Thus, suspensions with concentrations of 7% to 20% in a first step, 21% to 34% in a second step, 35% to 45% in a third step, 46% to 62% in a fourth step, 63% to 75% in a fifth step can be obtained. The yield of the final product is made from any step, as far as the necessary concentration is reached.

The method is based on the mechano-structural thixotropic properties of a dispersed system of hydroxylapatite which method consists in effecting reversible sol-gel transitions usually occuring upon mechanical stress by compulsory means.

It is noteworthy that the change of the structural mechanical, i.e. the thixotropic properties of disperse systems depend on the size and form of the particles forming this system. In rough disperse systems (particle sizes of 1 $\mu$m and more) the number of coagulation contacts is not sufficient to produce a sol and to effect the sol-gel transitions by means of mechanical stress. Therefore, the mechanical treatment of suspensions with particle sizes of 1 $\mu$m and more practically does not result in the change of its rheological properties.

The dimensions of the particles used in the synthesis of hydroxylapatite HAP are 0.01 $\mu$m to 0.02 $\mu$m in width and 0.05 $\mu$m to 0.1 $\mu$m in length permitting to utilize the thixotropic properties of the produced HAP suspension and to develope a method to specifically concentrate such suspensions. The mentioned dimensions and shapes of particles of the initial hydroxylapatite favour the formation of coagulation structures due to cohesion of the particles by Van der Waals forces interacting with links, chains, spatial nets, frameworks of the primary particles, their chains and aggregates. The centers of the point contacts appear at the ends of particles. Therefore, an anisometric, especially bar-like shape of the particles is favourable to from such structures. The afore-mentioned ratio between width and length of the particles of the initial HAP satisfies this requirement. Such systems are able to undergo reversible sol-gel transitions, i.e. to repeatedly form and destroy their structure.

Thus, it was found that during a stirring of the suspension having a concentration of 4.0% to 5.0% depending on the intensity and duration of stirring a partial or complete distruction of its structure occurs along with the transition of the sole into a gel. A subsequent filtration of the hydrogel results in a partial separation of the solvent (water) thereby concentrating the disperse system up to 7% to 20% and in the transition of the gel into a sol which has a spatial structure and stability formed at the expense of cohesion and aggregation of particles of the disperse phase, preventing its further filtration and concentration.

During further stirring the formed stable spatial structure depending on the intensity and duration of stirring is again partially or completely destroyed with the formation of a gel. The subsequent filtration of the hydrogel results in a partial and controlled separation of water, in concentrating the disperse system up to a concentration of 21% to 34% and the transition of the gel into a spatially structured and stable sol that practically prevents its further filtration and concentration. The same process occurs in all the subsequent stages of concentrating the suspension. The number of stages varies depending on the necessity to produce a suspension of a predetermined and required concentration.

From the above it can be seen, that the concentration of a suspension is a determining fact at each stage of the process. To adjust a desired concentration it is necessary to set specific conditions at the stage of stirring, e.g. rate and time, that in turn will depend on the type of the apparatus used, e.g. a tank with agitator, vibratory mill, vibrators with variable repetition and amplitude and so on and its volume. These parameters are selected in each case to produce a suspension of the desired concentration.

The method is illustrated by the following example(s).

EXAMPLE 1

554.6 g of anhydrous calcium oxide are introduced into a reactor containing distilled water at ambient temperature and distilled water is added until a solid/liquid ratio of S:L=1:35 is obtained. In a separate tank calcium hydroxide and the phosphoric acid in an amount that it is necessary to reach a pH of 10 are added. The residence time of the mixture in this tank is 1.0 s (the first zone).

Afterwards the mixture of the reaction products is supplied into the second tank (the second zone of reaction) where they are diluted with a suspension of calcium hydroxide by 400 times. The complete volume of the mixture containing calcium hydroxide and hydroxylapatite is circulated in a closed circuit combining the first and second zone. The circulating factor is 4. After this the phosphoric acid supply into the first zone is terminated and the suspension is stirred for 10 min.

As a result the pure stoichiometric hydroxylapatite in a suspension form is produced free of admixtures and having a hydroxylapatite concentration of 4.0% to 5.0%. The Ca/P ratio is 1.67 in the produced sample. The specific surface area is 100 m$^2$/g. The dimensions of the HAP crystals are 0.01 $\mu$m to 0.02 $\mu$m in width and 0.05 $\mu$m to 0.1 $\mu$m in length.

The produced suspension then is stirred for 7 min with the suspension flow rate equal to 0.8 m/s. Upon filtration a suspension (paste) with a concentration of 14.8% is prepared. Afterwards this suspension is stirred for 10 min with a suspension flow rate of 1.2 m/s and filtrated until a suspension (paste) with concentration of 26.6% is obtained. Then this suspension is again liquefied by means of agitation for 10 min at a suspension flow rate of 2 m/s and filtrated to produce a suspension (paste) with a concentration of 39.9%. The produced paste shows a homogeneous composition and homogeneous properties.

The conditions for producing suspensions of different concentrations may be illustrated by the following Table, where t is the time of treatment of the suspension in min, v is the stirring rate in m/s, C is the concentration of the HAP suspension based on the solid phase content in %, No. is the sample number and YP is the yield of the final product at the specified stage of the suspension processing.

The range of the agitation rate is determined by the aggregation degree of a suspension and by its concentration. At agitating rates lower than 0,8 m/s the sol destruction practically does not occur, even for suspensions of an initial concentration of 4% to 5% of HAP. At rates above 3.0 m/s the capturing of air bubles and aeration of the suspension deteriorating of the product quality occurs requiring additional operations to expel them.

The present invention allows to provide suspensions (pastes) of hydroxylapatite having a composition that is determined by the field of their application. Suspensions (pastes) of hydroxylapatite possess an improved quality. A selection of the product at any stage allows to produce suspensions or pastes in a wide range of concentrations from 7% to 96%, the produced pastes having a homogeneous composition that provides substantially easy conditions for their application and handling.

What is claimed is:

1. A hydroxylapatite (HAP) aqueous composition where the dimensions of the hydroxylapatite particles are 0.01 $\mu$m to 0.02 $\mu$m in width and 0.05 $\mu$m and 0.1 $\mu$m in length, the composition having a homogenous concentration within the range of from 7% to 96%.

2. The composition of claim 1 having a homogenous concentration of HAP between 7% to 20%.

3. The composition of claim 1, having a homogeneous concentration of HAP between 21% to 34%.

4. The composition of claim 1, having a homogeneous concentration of HAP between 35% to 45%.

5. The composition of claim 1, having a homogeneous concentration of HAP between 46% to 62%.

6. The composition of claim 1, having a homogeneous concentration of HAP between 63% to 75%.

7. The composition of claim 1 being in the form of a suspension.

8. The composition of claim 1 being in the form of a paste.

9. A method for preparing hydroxylapatite compositions wherein the dimension of the particles are in the range of 0.01 $\mu$m to 0.02 $\mu$m in width and 0.05 $\mu$m to 0.1 $\mu$m in length and with predeterminable homogeneous concentration ranges between 7% to 96%, wherein as a starting material a 4% to 5% aqueous composition of hydroxylapatite (HAP) consisting of the particle dimensions of 0.01 $\mu$m to 0.02 $\mu$m in width and 0.05 to 0.1 $\mu$m in length is subjected to alternating stirring and filtration stages with the stirring being carried out at a rate of from 0.8 m/s to 3.0 m/s for 5 min to 25 min, each stage thereby providing increasing homogeneous concentrations of HAP due to increasing stirring rates and/or times.

10. A denture material containing as a component a hydroxylapatite composition of claim 1.

11. A tooth paste containing as a component a hydroxylapatite composition of claim 1.

12. A chewing gum containing as a component a hydroxylapatite composition of claim 1.

13. A sorbent material for gas-liquid chromatography consisting of a hydroxylapatite composition of claim 1.

14. A method for using a hydroxylapatite (HAP) preparation in the field of stomatology comprising, using a hydroxylapatite (HAP) composition wherein the dimensions of the hydroxylapatite particles are 0.01 μm to 0.02 μm in length and 0.05 μm to 0.1 μm in width, the composition having a homogenous concentration within the range of from 7% to 96%. in the field of stomatology.

15. A method for using a hydroxylapatite (HAP) preparation in the field of bone surgery, comprising providing a hydroxylapatite (HAP) composition wherein the dimensions of the hydroxylapatite particles are 0.01 μm to 0.02 μm in length and 0.05 μm to 0.1 μm in width, the composition having a homogenous concentration within the range of from 7% to 96%, in the field of bone surgery.

16. A hydroxylapatite compositions wherein the dimension of the particles are in the range of 0.01 μm to 0.02 μm in width and 0.05 μm to 0.01 μm in length made by a process according to claim 9 comprising the steps of selecting a starting material of 4% to 5% aqueous composition of hydroxylapatite (HAP) consisting of the particle dimensions of 0.01 μm to 0.02 μm in width and 0.05 to 0.1 μm in lenght alternating stirring and filtration stages of said starting material with the stirring being carried out at a rate of from 0.8 m/s to 3.0 m/s for 5 min to 25 min, each stage thereby providing increasing homogeneous concentrations of HAP due to increasing stirring rates and/or times whereby the homogeneity of concentration is at least improved a decade to prior art concentrations of compositions of hydroxylapatite.

17. A method for using a hydroxylapatite (HAP) preparation in the field of stomatology, comprising using a hydroxylapatite (HAP) composition wherein the dimensions of the particles are in the range of 0.01 μm to 0.02 μm in width and 0.05 μm to 0.1 μm in length and with a predetermined homogenous concentration that ranges between 7% to 96%. wherein as starting material a 4% to 5% aqueous composition of hydroxylapatite (HAP) comprising particle dimensions of 0.01 μm to 0.02 μm in width and 0.05 to 0.1 μm in length is subjected to alternating stirring and filtration stages with the stirring being carried out at a rate of from 0.8 m/s to 3.0 m/s for 5 min to 25 min, each stage thereby providing increasing homogenous concentrations of said hydroxylapatite (HAP) due to increasing stirring rate and/or times, in the field of stomatology.

18. A method for using a hydroxylapatite (HAP) preparation in the field of bone surgery, comprising using a hydroxylapatite (HAP) composition wherein the dimensions of the particles are in the range of 0.01 μm to 0.02 μm in width and 0.05 μm to 0.1 μm in length and with a predetermined homogenous concentration that ranges between 7% to 96% wherein as starting material a 4% to 5% aqueous composition of hydroxylapatite (HAP) comprising particle dimensions of 0.01 μm to 0.02 μm in width and 0.05 to 0.1 μm in length is subjected to alternating stirring and filtration stages with the stirring being carried out at a rate of from 0.8 m/s to 3.0 m/s for 5 min to 25 min, each stage thereby providing increasing homogenous concentrations of said HAP composition due to increasing stirring rate and/or times, in the field of bone surgery.

19. A method for using a hydroxylapatite (HAP) composition as a component for producing denture material, comprising using a hydroxylapatite (HAP) composition wherein the dimensions of the particles are in the range of 0.01 μm to 0.02 μm in width and 0.05 μm to 0.1 μm in length, and with a predetermined homogenous concentration that ranges between 7% to 96%, wherein as starting material a 4% to 5% aqueous composition of hydroxylapatite (HAP) comprising particle dimensions of 0.01 μm to 0.02 μm in width and 0.05 to 0.1 μm in length is subjected to alternating stirring and filtration stages with the stirring being carried out at a rate of from 0.8 m/s to 3.0 m/s for 5 min to 25 min, each stage thereby providing increasing homogenous concentrations of HAP due to increasing stirring rate and/or times, in the field of denture material.

20. A method for using a hydroxylapatite (HAP) composition as a component for producing toothpastes comprising using a hydroxylapatite (HAP) composition, wherein the dimensions of the particles are in the range of 0.01 μm to 0.02 μm in width and 0.05 μm to 0.1 μm in length, and with a predetermined homogenous concentration that ranges between 7% to 96%, wherein as starting material a 4% to 5% aqueous composition of hydroxylapatite (HAP) comprising particle dimensions of 0.01 μm to 0.02 μm in width and 0.05 to 0.1 μm in length is subjected to alternating stirring and filtration stages with the stirring being carried out at a rate of from 0.8 m/s to 3.0 m/s for 5 min to 25 min, each stage thereby providing increasing homogenous concentration of HAP due to increasing stirring rate and/or times, in the field of toothpastes.

21. A method for using a hydroxylapatite (HAP) composition as a component for producing chewing gum, comprising providing a hydroxylapatite (HAP) composition wherein the dimensions of the particles are in the range of 0.01 μm to 0.02 μm in width and 0.05 μm to 0.1 μm in length, and with a predetermined homogenous concentration that ranges between 7% to 96%, wherein as starting material a 4% to 5% aqueous composition of hydroxylapatite (HAP), comprising particle dimensions of 0.01 μm to 0.02 μm in width and 0.05 to 0.1 μm in length is subjected to alternating stirring and filtration stages with the stirring being carried out at a rate of from 0.8 m/s to 3.0 m/s for 5 min to 25 min, each stage thereby providing increasing homogenous concentration of HAP due to increasing stirring rate and/or times, in the field of chewing gum.

22. A method for using a hydroxylapatite (HAP) composition as a component for producing sorbent material, comprising providing a hydroxylapatite (HAP) composition wherein the dimensions of the particles are in the range of 0.01 μm to 0.02 μm in width and 0.05 μm to 0.1 μm in length, and with a predetermined homogenous concentration that ranges between 7% to 96%, wherein as starting material a 4% to 5% aqueous composition of hydroxylapatite (HAP) comprising particle dimensions of 0.01 μm to 0.02 μm in width and 0.05 to 0.1 μm in length is subjected to alternating stirring and filtration stage with the stirring being carried out at a rate of from 0.8 m/s to 3.0 m/s for 5 min to 25 min, each stage thereby providing increasing homogenous concentration of HAP due to increasing stirring rate and/or times, in the field of sorbent material.

* * * * *